(12) United States Patent
Kihlberg et al.

(10) Patent No.: US 8,679,452 B2
(45) Date of Patent: Mar. 25, 2014

(54) MINIATURIZED LIQUID SURFACE REACTIONS USING NANOMOLAR AMOUNTS OF CONCENTRATED [$^{11}$C]CARBON DIOXIDE IN A STATIONARY GAS-PHASE

(75) Inventors: Tor Kihlberg, Uppsala (SE); Bengt Langstrom, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 656 days.

(21) Appl. No.: 12/158,712

(22) PCT Filed: Dec. 19, 2006

(86) PCT No.: PCT/IB2006/003700
§ 371 (c)(1),
(2), (4) Date: Oct. 29, 2008

(87) PCT Pub. No.: WO2007/072182
PCT Pub. Date: Jun. 28, 2007

(65) Prior Publication Data
US 2009/0092549 A1    Apr. 9, 2009

Related U.S. Application Data

(60) Provisional application No. 60/752,609, filed on Dec. 21, 2005.

(51) Int. Cl.
*A61K 51/00*        (2006.01)
*A61M 36/14*       (2006.01)

(52) U.S. Cl.
USPC ........................ 424/1.11; 424/1.81

(58) Field of Classification Search
None
See application file for complete search history.

(56) References Cited

U.S. PATENT DOCUMENTS 6,416,733 B1 *  7/2002  Barrett et al. ................ 424/1.65

FOREIGN PATENT DOCUMENTS

WO       02/102711       12/2002
WO       2005/042441      5/2005

OTHER PUBLICATIONS

Stocklin, G. (1993). Radiopharmaceuticals For Positron Emission Tomography. Dordrecht, The Netherlands: Kluwer Academic Publishers, p. 47-49.*
Davenport, R.J., et.al. "A simple technique for the automated product of no-carrier-added [1-(11)C] acetate" Applied Radiation and Isotopes, Elsevier, Oxford, GB, vol. 48, No. 8, Aug. 1997 pp. 1117-1120.
Schirbel, A. et.al. "N.C.a [11C]C02 as a safe substitute for phosgene in the carbonylation of primary amines" Journal of Labelled Compounds & Radiopharmaceuticals, vol. 42, No. 6, 1999 pp. 537-551.
Crouzel,C, et.al. "Recommendations for a practical production of [11C]methyl iodide" Int'l Journal of Radiation Applications and Instrumentation Part A: Applied Radiation and Isotopes, Pergamon Press Ltd., Exeter, GB, vo. 38, No. 8, 1987 pp. 601-603.
Celine P-H, et.al. "Reductive animation of carboxylic acids and [11C]magnesium halide carboxylations" Journal of the Chemical Society, Perkin Transactions 1, Chemical Society. Letchworth, GB 2000, pp. 311-316.
PCT/IB2006/003700 Int'l Search Report/Written Opinion dated Sep. 2007.

* cited by examiner

*Primary Examiner* — Michael G Hartley
*Assistant Examiner* — Melissa Perreira
(74) *Attorney, Agent, or Firm* — Jean K. Testa

(57) ABSTRACT

Methods and reagents for miniaturized carboxylation with carbon-isotope labeled carbon dioxide using Grignard reagents or other organometallic reagents in a closable reaction loop or reactor are provided. The resultant carbon-isotope labeled compounds are useful as radiopharmaceuticals or precursors for radiopharmaceuticals, especially for use in Positron Emission Tomography (PET). Associated kits for PET studies are also provided.

5 Claims, 2 Drawing Sheets

MINIATURIZED LIQUID SURFACE REACTIONS USING NANOMOLAR AMOUNTS OF CONCENTRATED [$^{11}$C]CARBON DIOXIDE IN A STATIONARY GAS-PHASE

CROSS-REFERENCE TO RELATED APPLICATIONS

This application is a filing under 35 U.S.C. §371 and claims priority to international patent application number PCT/IB2006/003700 filed Dec. 19, 2006, published on Jun. 28, 2007 as WO 2007/072182, which claims priority to application No. U.S. 60/752,609 filed Dec. 21, 2005.

FIELD OF THE INVENTION

The present invention relates to a method and an apparatus for the use of carbon-isotope dioxide in labeling synthesis. More specifically, the invention relates to a method and apparatus for producing an [$^{11}$C]carbon dioxide enriched gas mixture from an initial [$^{11}$C]carbon dioxide gas mixture, and using the produced gas mixture in labeling synthesis. Radiolabeled PET-tracers are provided using [$^{11}$C]carbon dioxide.

BACKGROUND OF THE INVENTION

Tracers labeled with short-lived positron emitting radionuclides (e.g. $^{11}$C, $t_{1/2}$=20.3 min) are frequently used in various non-invasive in vivo studies in combination with positron emission tomography (PET). Because of the radioactivity, the short half-lives and the submicromolar amounts of the labeled substances, extraordinary synthetic procedures are required for the production of these tracers. An important part of the elaboration of these procedures is development and handling of new $^{11}$C-labelled precursors. This is important not only for labeling new types of compounds, but also for increasing the possibility of labeling a given compound in different positions.

In $^{11}$C-labelling synthesis [$^{11}$C]carbon dioxide is the most versatile of the primary precursors (radionuclide labeled compound obtained in a target) with respect to production yield, ease of separation from target gas and prospect for chemical transformation. [$^{11}$C]Carbon dioxide, is readily obtained from the N(p,α)$^{11}$C reaction by presence of low concentrations of oxygen. It is particularly useful in reactions with organo lithium compounds and Grignard reagents which give access to important tracers such as acetate and palmitate labeled in the carboxylic position. Carboxylation reactions using [$^{11}$C]carbon dioxide has a primary value for PET-tracer synthesis since biologically active substances often contain a carboxyl group or functionalities that can be derived from a carboxyl group.

The reaction of [$^{11}$C]carbon dioxide with a Grignard reagent followed by reduction with lithium aluminum hydride (LAH) and finally iodination with hydroiodic acid is a versatile method for synthesis of $^{11}$C-labelled organo iodides. The $^{11}$C-labelled organo iodides are valuable precursors that can be used for the labeling of a broad range of biological active compounds. There are, however, several problems associated with this method. The Grignard reagents usually contains the corresponding non radioactive compound, from reaction with atmospheric carbon dioxide, which leads to isotopic dilution and decrease of the specific radioactivity. In order to minimize the isotopic dilution and facilitate automation, the use miniaturization and reagent coated reaction loops are valuable approaches. In the case of higher boiling organo iodides such as benzyl iodide the recovery from the hydroiodic acid has to be performed using extraction; an operation that is relative difficult to automate. Miniaturization and the use of reaction loop techniques is one way to circumvent the problems.

When prior art was applied in the synthesis of [$^{11}$C]benzyl iodide using phenyl magnesium bromide coated on a reaction loop, the elution of the [$^{11}$C]benzoate from the loop using diethyl ether failed. The reason was that the Grignard reagent precipitated during the transfer of the [$^{11}$C]carbon dioxide and encapsulated the [$^{11}$C]benzoate. The use of diethyl ether was a necessary requirement for the succeeding LAH-reduction and hydro iodination reaction.

In a similar investigation [$^{11}$C] acetate was synthesized using a reaction loop coated with methyl magnesium bromide and [$^{11}$C]carbon dioxide handled with prior art. The results suffered from bad reproducibility, low trapping efficiency of [$^{11}$C]carbon dioxide and high levels of the side products [$^{11}$C]acetone and [$^{11}$C]tert-butanol.

In most previous methods the relative large volume of gas used for carrying the [$^{11}$C]carbon dioxide has been allowed to flow through the reaction compartment and the [$^{11}$C]carbon dioxide has been trapped solely by the process of conversion to products. There are several drawbacks and limitations with this method.

- The trapping efficiency is determined by the amount and concentration of the reagent (e.g. Grignard reagent). This limit the possibilities for miniaturization and simplification (e.g. omit purification). A high concentration of the reagent may also lead to increased side reactions (e.g. in the synthesis of [1-$^{11}$C]acetate further addition of methyl magnesium bromide will give [$^{11}$C]acetone and [$^{11}$C]tert-butanol as side products).
- The flow of carrier gas through the reaction compartment will, in the case volatile solvents are used, lead to evaporation of solvent, which will lead to an increased concentration and possible precipitation of the reagent. This may lead to increased side reactions and difficulties in subsequent eluting the radioactive product from the compartment.
- Due to the relative large volume of carrier gas and the need of using a relative low flow during the transfer of [$^{11}$C] carbon dioxide in order to obtain high trapping efficiency, the time span of the transfer is long. This may lead to a distribution in reaction time for the batch of [$^{11}$C]carbon dioxide with several 100%.
- If weakly reactive reagents are used, that requires several minutes for conversion of the [$^{11}$C]carbon dioxide, the fraction of the radioactivity that will be trapped by passage through the reagent will be low.

When compounds are labeled with $^{11}$C, it is usually important to maximize specific radioactivity. In order to achieve this, the isotopic dilution and the synthesis time must be minimized. Isotopic dilution from atmospheric carbon dioxide may be substantial when [$^{11}$C]carbon dioxide is used in a labeling reaction and is usually proportional to the amount of reagent. Miniaturization of synthesis equipment and minimization of the amounts of reagents is an important approach for increase of specific radioactivity in this context.

The cold-trap technique is widely used in the handling of $^{11}$C-labelled precursors, particularly in the case of [$^{11}$C]carbon dioxide. The procedure has, however, only been performed in one single step and the labeled compound was always released in a continuous gas-stream simultaneous with the heating of the cold-trap. Thus, the option of using this technique for radical concentration of the labeled compound and miniaturization of synthesis systems has not been explored. This is especially noteworthy in view of the fact that the amount of a $^{11}$C-labelled compound usually is in the range 20-60 nmol.

Discussion or citation of a reference herein shall not be construed as an admission that such reference is prior art to the present invention.

SUMMARY OF THE INVENTION

The present invention provides a method for labeling synthesis, comprising:
(a) providing a reagent volume to be labeled,
(b) providing carbon-isotope dioxide in a carrier gas,
(c) concentrating carbon-isotope dioxide by trapping in a miniaturized column,
(d) introducing and confining carbon-isotope dioxide enriched gas-mixture into the reaction chamber via a gas inlet while having the outlet of the reaction chamber closed,
(e) waiting for a predetermined period of time,
(f) collecting the labeled product from the reaction chamber.

The present invention further provides a method for the synthesis of labeled organo halides using subsequent reduction and halogenation.

In yet another embodiment, the invention also provides $^{11}$C-labeled carboxylic acids or organo halides. In still another embodiment, the invention provides kits for use as PET tracers comprising carboxylic acids or compounds derived from organo halides labeled with $^{11}$C.

DETAILED DESCRIPTION OF THE INVENTION

The object of the invention is to provide a method and a system for concentration and use of carbon-isotope dioxide in labeling synthesis that overcomes the drawbacks of the prior art devices. This is achieved by the method and system claimed in the invention. The most important and novel aspects of the invention is the miniaturization of the carbon dioxide trapping device, which concentrates carbon isotope dioxide, and that the flow through the trapping device is stopped during heating when the carbon isotope dioxide is released from the active surface of the trapping device. The latter ensures that the dilution of the concentrated carbon isotope dioxide is minimized at the transfer to the reaction compartment.

There are several advantages with the present method and system.

The concentration of the reagent in the reaction chamber (e.g. coated on the internal surface of the loop) is not altered during the transfer and reaction of [$^{11}$C]carbon dioxide.

The transfer of [$^{11}$C]carbon dioxide to the reaction compartment (e.g. a loop) is achieved in a few seconds. Thus the start of reaction time will be sharp for all [$^{11}$C]carbon dioxide that is transferred.

The amount of reagent can be reduced since the [$^{11}$C] carbon dioxide is confined in the reaction compartment until it is consumed in the reaction.

The conversion of [$^{11}$C]carbon dioxide to products (trapping efficiency) will be high also in case reagents of low reactivity are used.

The reason is that the [$^{11}$C]carbon dioxide can be enclosed with the reagent until it is consumed.

The use of a closed system consisting of materials that prevents gas diffusion increases the stability of sensitive compounds and could be advantageous also with respect to Good Manufacturing Practice (GMP).

Still other advantages are achieved in that the resulting labeled compound is highly concentrated, and that the miniaturization of the synthesis system facilitates automation, rapid synthesis and purification, and optimization of specific radioactivity through minimization of isotopic dilution.

Embodiments of the invention will now be described with reference to the figures.

The term carbon-isotope that is used throughout this application preferably refers to $^{11}$C, but it should be understood that $^{11}$C may be substituted by other carbon-isotopes, such as $^{13}$C and $^{14}$C, if desired.

Figure 1:
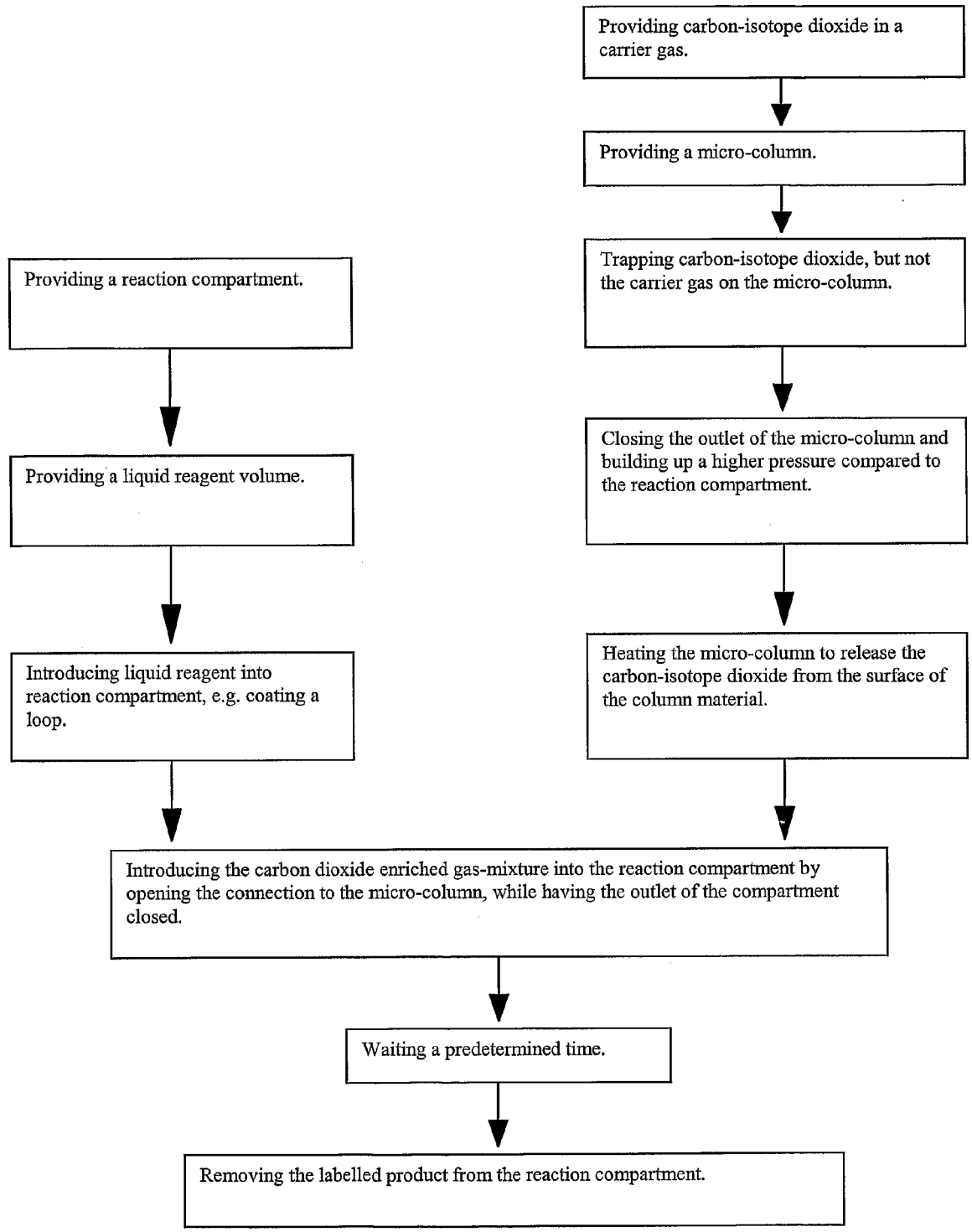
FIG. 1 shows a flow chart over the method according to the invention.

FIG. 1 shows a flow chart over the method according to the invention, which firstly comprises production of a carbon-isotope dioxide enriched gas-mixture and secondly a labeling synthesis procedure. More in detail the production part of the method comprises the steps of:
Providing carbon-isotope dioxide in a suitable carrier gas of a type that will be described in detail below.
Concentrating carbon-isotope dioxide by trapping in a miniaturized column device which will be described in detail below.
Releasing said trapped carbon-isotope monoxide from said trapping device, whereby a volume of carbon-isotope dioxide enriched gas-mixture is achieved.

The production step may further comprise a step of changing carrier gas for the initial carbon-isotope dioxide gas mixture if the initial carbon-isotope dioxide gas mixture is comprised of carbon-isotope dioxide and a first carrier gas not suitable as carrier gas. More in detail the step of providing carbon-isotope dioxide in a suitable carrier gas such as He, Ar, comprises the steps of:
Flushing said carbon dioxide trapping device with said suitable second carrier gas to remove the remainders of said first carrier gas.
Releasing said trapped carbon-isotope dioxide in said suitable second carrier gas.

The labeling synthesis step that may follow the production step utilizes the produced carbon-isotope dioxide enriched gas-mixture as labeling reactant. More in detail the step of labeling synthesis comprises the steps of:
Providing a reaction chamber (e.g. loop reactor) assembly comprising a reaction chamber and valves.
Providing a liquid reagent volume that is to be labeled. Suitable samples are discussed above.
Introducing the carbon-isotope dioxide enriched gas-mixture into the reaction chamber via the gas (labeling reactant) inlet.
Waiting for a predetermined period of time.
Collecting the solution of labeled product from the reaction chamber.

The step of waiting a predetermined time may further comprise adjusting the temperature of the reaction chamber such that the labeling synthesis is enhanced.

Figure 2:
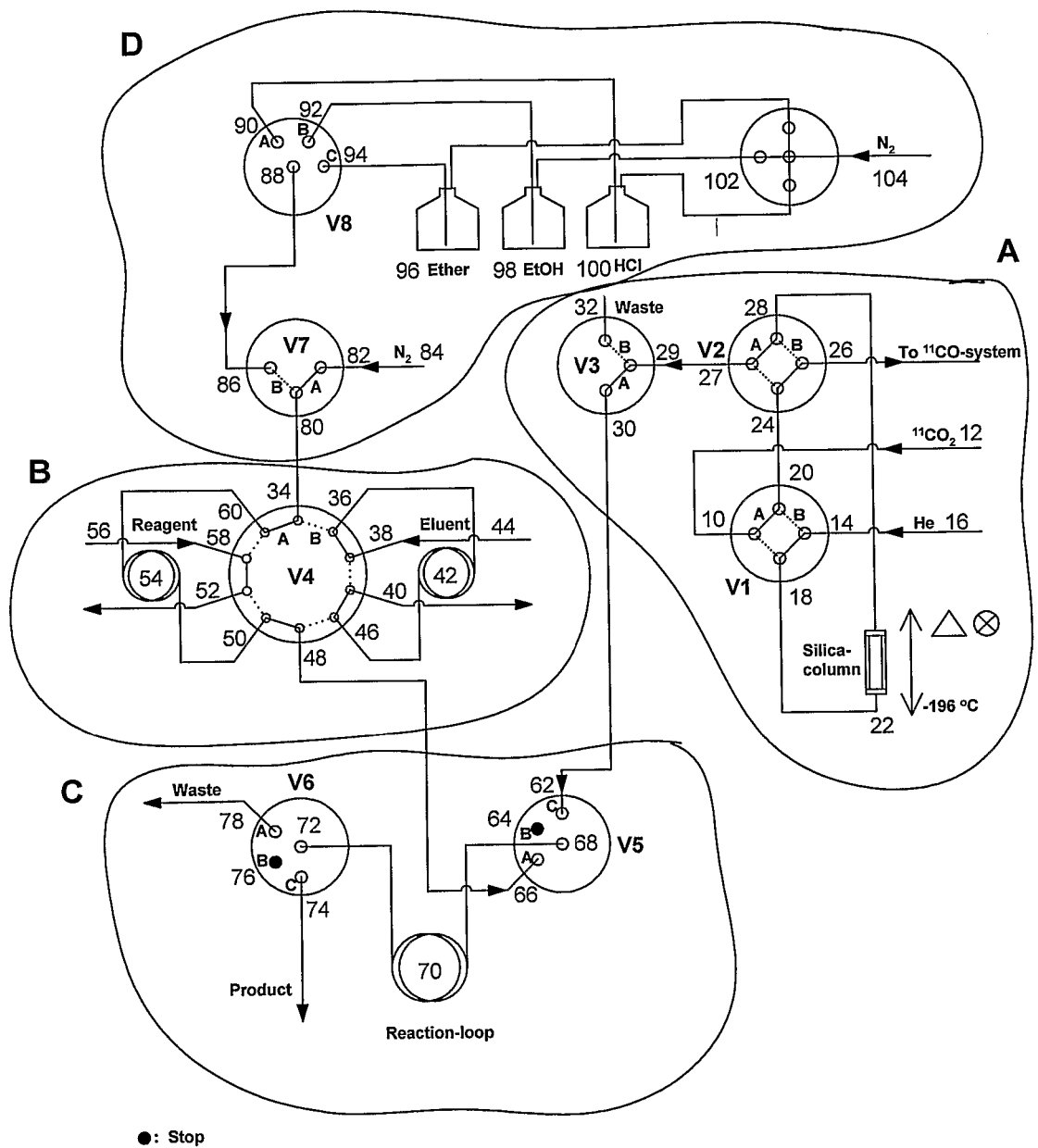
FIG. 2 is a schematic view of a carbon-isotope dioxide production and labeling-system according to the invention.

FIG. 2 schematically shows a [$^{11}$C]carbon dioxide concentration and labeling-system according to the present invention. The system is comprised of three main blocks, each handling one of the three main steps of the method of production and labeling:

Block A is used for concentration and pressurization of carbon-isotope dioxide.

Block B is used for loading reagents and elution agents in loops for transfer through the reaction loop of block C.

Block C is used to perform the carbon-isotope dioxide labeling synthesis.

Block D is used for automated washing of block B and C.

According to a preferred embodiment (FIG. 2), block A is comprised of a first valve V1, a carbon dioxide trapping device 22, and a second and a third valve V2 and V3.

The first valve V1 has a carbon dioxide inlet 10 connected to a source of initial carbon-isotope dioxide gas mixture 12, a carrier gas inlet 14 connected to a source of suitable carrier gas 16, such as helium, argon and the like. The first valve V1 further has a first outlet 20 connected to a first inlet 24 of the second valve V2, and a second outlet 18 connected to the carbon dioxide trapping device 22. The valve V1 may be operated in two modes A, B, in mode A the carbon dioxide inlet 10 is connected to the first outlet 20 and the carrier gas inlet 14 is connected to the second outlet 18, and in mode B the carbon dioxide inlet 10 is connected to the second outlet 18 and the carrier gas inlet 14 is connected to the first outlet 20.

In addition to the first inlet 24, the second valve V2 has a second inlet 28 connected to the carbon dioxide trapping device 22. The second valve V2 further has an outlet 26 connected to e.g. a system for production and use of $[^{11}C]$ carbon monoxide, and an outlet 27 connected to inlet 29 of valve V3. The valve V2 may be operated in two modes A, B, in mode A the first inlet 24 is connected to the outlet 26 and the second inlet 28 is connected to the outlet 27, and in mode B the first inlet 24 is connected to the outlet 27 and the second inlet 28 is connected to the outlet 26.

The carbon dioxide trapping device 22 is a device wherein carbon dioxide is trapped but not said first carrier gas, which trapped carbon dioxide thereafter may be released in a controlled manner. This may preferably be achieved by using a cold trap, such as a column containing a material which in a cold state, (e.g. $-196°$ C. as in liquid nitrogen or $-186°$ C. as in liquid argon) selectively trap carbon dioxide and in a warm state (e.g. $+50°$ C.) releases the trapped carbon dioxide. (In this text the expression "cold trap" is not restricted to the use of cryogenics. Thus, materials that trap the topical compound at room temperature and release it at a higher temperature are included). One suitable material is silica. The trapping behavior of a silica-column is related to dipole-dipole interactions or possibly Van der Waal interactions. The said column 22 is preferably formed such that the volume of the trapping material is to be large enough to efficiently trap (>95%) the carbon-isotope dioxide, and small enough not to prolong the transfer of trapped carbon dioxide to block C. In the case of silica and a flow of 100 ml nitrogen/min, the volume should be 0.5-3 µl. The cooling and heating of the carbon dioxide trapping device 22 may further be arranged such that it is performed as an automated process, e.g. by automatically lowering the column into liquid nitrogen and moving it from there into a heating arrangement. An alternative is spraying liquid nitrogen on the column for cooling and then blowing hot air on the column for heating.

According to the preferred embodiment of FIG. 2, block C is comprised of a reactor chamber 70 in which carbon-isotope dioxide is reacted with a reagent.

In the preferred embodiment the reaction chamber 70 is loop made of nickel tubing with an internal volume of 50 to 500 µL.

According to the preferred embodiment of FIG. 2, block C is comprised of a first and a second reaction chamber valve V5 and V6, and a reaction loop or reaction chamber.

The first reaction loop valve V5 has a gas mixture inlet 62 connected to outlet 30 of valve V3 of block A, a stop position 64, a gas and liquid inlet 66 connected to outlet 48 of valve V4 of block B and an outlet 68 connected to the reaction chamber 70. The second reaction loop valve V6 has an inlet 72 connected to the reaction chamber 70, a waste outlet 78, a stop position 76 and a product outlet 74.

According to the preferred embodiment of FIG. 2, block B is comprised of a ten ports Valve V4 and two attached reservoir loops.

Valve V4 has an inlet 34 connected to the outlet 80 of valve V7 of block D. An eluent loop 42 is connected to 36 and 46 with the feed of eluent liquid 44 connected to 38 and the waste outlet connected to 40. A reagent loop 54 is connected to 50 and 60 with the feed of reagent liquid 56 connected to 58 and the waste outlet connected to 52. The outlet 48 is connected to the inlet 66 of valve V5 of block C. The valve V4 may be operated in two modes A and B. In mode A the content of loop 54 can be transferred to block C using pressurized gas or liquid from block D. In mode B the content of loop 42 can be transferred to block C using pressurized gas or liquid from block D. In mode A loop 42 can be loaded via inlet 38 and in mode B loop 54 can be loaded via inlet 58.

According to a preferred embodiment (FIG. 2), block D is comprised of a first valve V8, a set of reservoir flask 96, 98 and 100, a gas manifold 102, and a second valve V7.

Valve V7 has an inlet 82 for nitrogen 84, an inlet 86 connected to the outlet 88 of valve V8. The valve V7 may be operated in two modes A and B. In mode A the nitrogen 84 is directed to the outlet 80, in mode B liquid from valve V8 is directed to outlet 80. Valve V8 has an inlet 90 connected to flask 100, an inlet 92 connected to flask 98, an inlet 94 connected to flask 96. Valve V8 may be operated in three modes A, B and C. In mode A the outlet 88 is connected to flask 100, in B to flask 98 and in C to flak 96. The nitrogen 104 being fed into the manifold 102 is directed to and pressurizing flask 96, 98 and 100.

Except for the small volume of silica in the carbon dioxide trapping devise 22, an important difference in comparison to all related prior art, is the procedure used for releasing the carbon dioxide. After the trapping of carbon dioxide on carbon dioxide trapping devise 22, valve V3 is changed from position B to A and valve V5 is set in position B with inlet 62 stopped. The flow from the carbon dioxide trapping devise 22 is thus stopped and the gas-pressure on the carbon dioxide trapping devise 22 will rapidly reach the set feeding gas pressure (3-5 bar). Valve V6 is set to position B and the outlet of reaction chamber 70 is thus stopped. The carbon dioxide trapping devise 22 is then heated to release the carbon dioxide from the silica surface while not significantly expanding the volume of carbon dioxide in the carrier gas. Valve V5 is changed from position B to C. At this instance the carbon dioxide is rapidly and almost quantitatively transferred in a well-defined micro-plug into the reaction loop 70. Micro-plug is defined as a gas volume less than 10% of the volume of the reaction loop 70, containing the topical substance (e.g. 1-20 µL). This unique method for efficient mass-transfer to a small reaction chamber 70, having a closed outlet, has the following prerequisites:

A micro-column 22 defined as follows should be used. The volume of the trapping material (e.g. silica) should be large enough to efficiently trap (>95%) the carbon-isotope dioxide, and small enough (<1% of the volume of a subsequent reaction chamber 70) to allow maximal concentration of the carbon-isotope monoxide. In the case of silica and a reaction loop 70 volume of 200 μL, the silica volume should be 0.1-2 μL.

The dead volumes of the tubing and valve(s) connecting the silica column and the reaction chamber 70 should be minimal (<10% of the loop volume).

The pressure of the carrier gas should be 3-5 times higher than the pressure in the reaction chamber 70 before transfer (1 atm.).

In one specific preferred embodiment specifications, materials and components are chosen as follows. High pressure valves from Valco®, Reodyne® or Cheminert® are used. Stainless steel tubing with o.d. 1/16" is used except for the connections to the, the silica-column 22 where stainless steel tubing with o.d. 1/32" are used in order to facilitate the translation movement. The connections between 10 to 12, 14 to 16 and 18 to 22 should have an inner diameter of 0.2-1 mm. The requirement is that the inner diameter should be large enough not to obstruct the possibility to achieve the optimal flow of He (2-200 ml/min) through the system, and small enough not to prolong the time needed to transfer the radioactivity to the silica-column 22. The dead volume of the connection between 22 and the reaction loop 70 should be minimized (<10% of the loop volume). The inner diameter (0.05-0.1 mm) of the connection must be large enough to allow optimal He flow (2-50 ml/min).

The silica-column 22 preferably is comprised of a stainless steel tube (o.d.=1/16", i.d.=0.1 mm) with a cavity (d=1 mm, h=1 mm, V=0.8 μL) in the end. The cavity is filled with silica powder (100/80 mesh) of GC-stationary phase type. The end of the column is fitted against a stainless steel screen.

It should be noted that a broad range of different materials could be used in the trapping devices. If a GC-material is chosen, the criterions should be good retardation and good peak-shape for carbon dioxide. The latter will ensure optimal recovery of the radioactivity.

Below a detailed description is given of a method of producing a carbon-isotope labeled compound using an exemplary system as described above.

Preparations of the system are performed by the steps 1 to 5:

1. V6 in position A, V5 in position B, V4 in position B, V7 in position A, nitrogen flow 84 on with a max pressure of 2 bar. Loop 54 is loaded with Reagent. V4 in position A. Loop 42 is loaded with eluent.
2. V5 in position A. The reagent is allowed to pass and coat the reaction loop 70. V5 in position B and then V6 in position B.
3. V3 in position B, V1 in position B, V2 in position A.
4. The silica-column 22 is cooled with liquid nitrogen. At −196° C., the silica-column efficiently traps carbon-isotope dioxide.
5. Carbon-isotope dioxide is produced using the $^{14}N(p,\alpha)$ $^{11}C$ reaction in a target gas containing nitrogen (AGA, Nitrogen 6.0) and 0.1% oxygen (AGA. Oxygen 4.8), bombarded with 17 MeV protons.
6. Carbon-isotope dioxide in a carrier gas is directed to inlet 10 and trapped in silica-column 22.
7. V1 in position A and V3 in position A.
8. The silica-column 22 is heated to approximately 50° C., which releases the carbon-isotope dioxide. V5 is set to position C and the carbon-isotope dioxide is transferred to the reaction chamber 70 within 15 s.
9. After a sufficient reaction-time (usually 1 min), V6 is set to position C and V5 to position A. At this instant the content of loop 42 is transferred through the reaction chamber 70 eluting the radioactivity via outlet 74 to a collection vial.
10. Block B and C can be washed by the following procedure: V6 is set to position C, V5 is set to position A, V7 is set to position B, V8 is set to position A. Diluted hydrochloric acid is allowed to flow through block B and C. Valve V7 is alternated between mode A and B with a frequency of about 0.2 Hz. Valve V4 is set to position A for about 30 s and at position B for about 30 s. Likewise valve V6 is set to both position A and C. The same procedure is repeated with valve V8 in position B and C respectively.

With the fully automated version of the [$^{11}$C]carbon dioxide concentration unit in combination with the closable reaction unit according to the invention, the value of [$^{11}$C]carbon dioxide as a precursor for $^{11}$C-labelled tracers has increased. The higher reproducibility and radiochemical yields give the option of using a single tracer production for several PET investigations (patients) or transfer to remote facilities.

The following reactions are included in the invention.

Scheme 1.

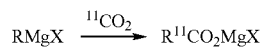

R = an alkyl or aryl group that could contain the following functional groups: F, Cl, alkoxy, aryloxy, chalcogen ethers, alkene, alkyne, tertiary amine. X = halogen.

Scheme 2.

R = alkyl or aryl group that could contain the following functional groups: alkoxy, aryloxy, chalcogen ethers, alkene, alkyne, tertiary amine. X = halogen. Q = H or $^2$H. Z = Br, I.

Scheme 3.

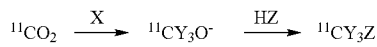

X = hydride, deuteride reduction agent e.g. lithium aluminum hydride. Z = Br, I. Y = H or $^2$H.

Scheme 4.

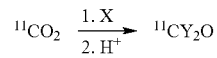

X = hydride, deuteride reduction agent e.g. lithium aluminum hydride. Y = H or $^2$H.

Scheme 5.

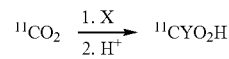

X = hydride, deuteride reduction agent e.g. lithium aluminum hydride. Y = H or $^2$H.

Scheme 6.

R = alkyl or aryl group that could contain the following functional groups: halogens, alkoxy, aryloxy, chalcogen ethers, alkene, alkyne, tertiary amine, carbonyl groups. X = dehydration reagent such as $POCl_3$.

Scheme 6.

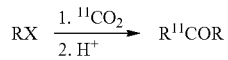

R = alkyl or aryl group that could contain the following functional groups: F, Cl, alkoxy, aryloxy, chalcogen ethers, alkene, alkyne, tertiary amine. X = metal or metal containing group such as: Li and MgX were X is a halogen.

Scheme 7.

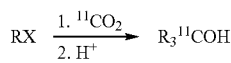

R = alkyl or aryl group that could contain the following functional groups: F, Cl, alkoxy, aryloxy, chalcogen ethers, alkene, alkyne, tertiary amine. X = metal or metal containing group such as: Li and MgX were X is a halogen.

The resultant carbon-isotope labeled compounds are useful as radiopharmaceuticals or precursors for radiopharmaceuticals. They provide valuable PET tracers in various PET studies. In an embodiment of the present invention, it provides kits for use as PET tracers comprising [$^{11}$C]-labeled compounds.

Such kits are designed to give sterile products suitable for human administration, e.g. direct injection into the bloodstream. Suitable kits comprise containers (e.g. septum-sealed vials) containing the [$^{11}$C]-labeled compounds.

The kits may optionally further comprise additional components such as radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e., ethyl, propyl or butyl paraben or mixtures thereof, benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

Furthermore, through the use of similar technology, this method will most likely be applicable for synthesis of $^{13}$C and $^{14}$C substituted compounds.

EXAMPLES

The invention is further described in the following examples which are in no way intended to limit the scope of the invention.

TABLE 1

Carboxylic acids that can be synthesized using the invention.

$R^XCO_2H$
R = alkyl or aryl group that could contain the following functional groups: F, Cl, alkoxy, aryloxy, chalcogen ethers, alkene, alkyne, tertiary amine.
X = 11, 13, 14

TABLE 2

Organo halides that can be synthesized using the invention.

$R^XCH_2Z$
R = alkyl or aryl group that could contain the following functional groups: alkene or alkyne.
X = 11, 13, 14.
Z = Br, I

Example 1

Experimental Setup

[$^{11}$C]Carbon dioxide production was performed using a Scanditronix MC-17 cyclotron at Uppsala IMANET. The $^{14}$N(p,α)$^{11}$C reaction was employed in a gas target containing nitrogen (Nitrogen 6.0) and 0.1% oxygen (Oxygen 4.8) which was bombarded with 17 MeV protons.

The syntheses with [$^{11}$C]carbon dioxide were performed with an automated module as part of the system "Synthia 2000".

Liquid chromatographic analysis (LC) was performed with a gradient pump and a variable wavelength UV-detector in series with a β$^+$-flow detector. The following mobile phases were used: 25 mM potassium dihydrogenphosphate (A) and acetonitrile/$H_2O$: 50/7 (B). For analytical LC, a $C_{18}$, 4 μm, 250×4.6 mm ID column was used at a flow of 1.5 mL/min. For semi-preparative LC, a $C_{18}$, 4 μm, 250×10 mm (i.d.), column was used at a flow of 4 mL/min. An automated synthesis system, Synthia was used for LC injection and fraction collection.

Radioactivity was measured in an ion chamber, Veenstra Instrumenten bv, VDC-202.

In the analysis of the $^{11}$C-labeled compounds, unlabeled reference substances were used for comparison in all the LC runs.

LC-MS analysis was performed using a Micromass VG Quattro with electrospray ionization. A Beckman 126 pump, a CMA 240 autosampler were used.

THF and diethyl ether was distilled under nitrogen from sodium/beizophenone. All starting materials were commercially available.

Example 2

Preparation of [1-$^{11}$C]Acetate

The reagent loop 54 was loaded with methyl magnesium bromide (0.5 mL, 0.5 M in diethyl ether) and the eluent loop 42 was loaded with hydrochloric acid (0.5 mL, 0.3 M in water). The labelling procedure was performed as described above and the [$^{11}$C] carbon dioxide was allowed to react for 1 min in the reaction loop with the methyl magnesium bromide.

The crude reaction mixture was transferred from the reaction loop 70 to a capped vial (2 mL). The vial was purged with nitrogen and the crude product was diluted with saline (0.5 mL) and injected on the semi-preparative LC. Analytical LC was used to assess the identity and radiochemical purity of the collected fraction.

Example 3

Preparation of [1-$^{11}$C]Palmitate

The reagent loop 54 was loaded with pentadecyl magnesium bromide (0.5 mL, 0.5 M in diethyl ether) and the eluent loop 42 was loaded with an acetonitrile hydrochloric acid mixture (0.5 mL, 10% (1 M HCl in water) in acetonitrile). The labelling procedure was performed as described above and the [$^{11}$C]carbon dioxide was allowed to react for 2 min in the reaction loop with the pentadecyl magnesium bromide.

The crude reaction mixture was transferred from the reaction loop 70 to a capped vial (2 mL). The vial was purged with nitrogen and the crude product was diluted with a water acetonitrile mixture (1:1, 0.5 mL) and injected on the semi-preparative LC. Analytical LC was used to assess the identity and radiochemical purity of the collected fraction.

Example 4

Preparation of [1-$^{11}$C]Benzyl Iodide

The reagent loop 54 was loaded with phenyl magnesium bromide (0.5 mL, 0.5 M in toluene) and the eluent loop 42 was loaded with diethyl ether (0.5 mL). The labelling procedure was performed as described above and the [$^{11}$C]carbon dioxide was allowed to react for 1 min in the reaction loop with the phenyl magnesium bromide.

The crude reaction mixture was transferred from the reaction loop 70 to a capped vial (2 mL) containing lithium aluminum hydride (30 mL, 1 M in diethyl ether). The vial was heated at 110° C. for 1 min and was then purged with nitrogen for 30 s. Hydroiodic acid (0.4 mL, 57% in water) was added and the resulting mixture was heated at 110° C. for 1 min. The mixture was diluted with water (1 mL) and pressed trough a solid phase extraction column (Bond Elut ENV from Varian, 25 mg in a 1 mL cartridge). The SPE column was washed with water (5 mL) and purged with nitrogen (500 mL/min for 30 s). The SPE column was eluted with toluene (0.5 mL) and the eluent was allowed to pass a drying tower (a 1 mL empty SPE cartridge loaded from the bottom upwards: 1. a frit 2. $K_2CO_3$ (anhydrous, 6 mm) 3. a frit 4. Sicapent® (6 mm) 5. a frit 6. $Na_2S_2O_3$ (6 mm). The drying tower is then conditioned with toluene (3 mL) before use.)

Analytical LC was used to assess the identity and radiochemical purity of the [1-$^{11}$C]benzyl iodide.

Example 5

Preparation of [$^{11}$C]Methyl Iodide

The reagent loop 54 was loaded with lithium aluminium hydride (0.5 mL, 0.2 M in tetrahydrofurane) and the eluent loop 42 was loaded with hydroiodic acid (0.2 mL). The labelling procedure was performed as described above and the [$^{11}$C]carbon dioxide was allowed to react for 0.5 min in the reaction loop with the lithium aluminium hydride.

The labeled metoxide was transferred from the reaction loop 70 to a reactor (2 mL) heated at 60° C. The vial was rapidly heated to 130° C. for 1 min and the reaction mixture was purged with nitrogen to transfer the formed [$^{11}$C]methyl iodide via drying tower containing Sicapent® (2 g) into a vial containing DMF (0.3 ml).

Analytical LC was used to assess the identity and radiochemical purity of the [$^{11}$C]methyl iodide.

SPECIFIC EMBODIMENTS, CITATION OF REFERENCES

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for labeling synthesis, comprising:
   (a) providing a reagent volume to be labeled in a reaction chamber,
   (b) providing carbon-isotope dioxide in a carrier gas,
   (c) concentrating carbon-isotope dioxide by trapping in a carbon dioxide trapping device to generate a carbon-isotope dioxide enriched gas-mixture, wherein the trapping device has an outlet which is closed and a high pressure compared to the reaction chamber is built up in the trapping device,
   (d) introducing and confining the carbon-isotope dioxide enriched gas-mixture into said reaction chamber via a gas inlet, said reaction chamber has an outlet which is closed,
   (e) waiting for a predetermined time while the labeling synthesis occur, and
   (f) collecting the labeled product from the reaction chamber.

2. A method of claim 1, wherein the carbon-isotope dioxide enriched gas-mixture is produced by a method comprising:
   (a) providing carbon-isotope dioxide in a suitable carrier gas,
   (b) trapping carbon-isotope dioxide in the carbon dioxide trapping device, wherein carbon-isotope dioxide is trapped but not said carrier gas, and (c) releasing said trapped carbon-isotope dioxide from said trapping device in a well defined micro-plug, whereby a volume of carbon-isotope dioxide enriched gas-mixture is achieved.

3. A method of claim 1, wherein the suitable carrier gas is He or Ar.

4. A method of claim 1, wherein the carbon-isotope is $^{11}C$.

5. A method of claim 1, wherein the step of waiting a predetermined time comprises heating reaction chamber to enhance the labeling synthesis.

\* \* \* \* \*